United States Patent
Elshaer (10) Patent No.: US 11,603,437 B2
(45) Date of Patent: Mar. 14, 2023

(54) PHOTODYNAMIC CATIONIC PORPHYRIN COMPOSITES

(71) Applicant: Fairleigh Dickinson University, Teaneck, NJ (US)

(72) Inventor: Mohammed R. Elshaer, River Vale, NJ (US)

(73) Assignee: Fairleigh Dickinson University, Teaneck, NJ (US)

(*) Notice: Subject to any disclaimer, the term of this patent is extended or adjusted under 35 U.S.C. 154(b) by 248 days.

(21) Appl. No.: 16/995,188

(22) Filed: Aug. 17, 2020

(65) Prior Publication Data

US 2021/0047477 A1    Feb. 18, 2021

Related U.S. Application Data

(60) Provisional application No. 62/887,808, filed on Aug. 16, 2019.

(51) Int. Cl.
| | | |
|---|---|---|
| *C08G 83/00* | (2006.01) | |
| *C07D 487/22* | (2006.01) | |
| *C02F 1/32* | (2023.01) | |
| *C02F 1/72* | (2023.01) | |
| *C02F 101/30* | (2006.01) | |

(52) U.S. Cl.
CPC ............. *C08G 83/001* (2013.01); *C02F 1/32* (2013.01); *C02F 1/725* (2013.01); *C07D 487/22* (2013.01); *C02F 2101/30* (2013.01); *C02F 2303/04* (2013.01); *C02F 2305/023* (2013.01); *C02F 2305/10* (2013.01)

(58) Field of Classification Search
CPC ..... C02F 1/30; C02F 1/32; C02F 1/50; C08G 83/001; C07D 487/22
See application file for complete search history.

(56) References Cited

FOREIGN PATENT DOCUMENTS

WO    WO-2006118542 A1 * 11/2006 ............... B82B 1/00

OTHER PUBLICATIONS

Wodzinski, Rebecca et al.; Photosensitizing antimicrobial polymer solid-state composites for water treatment; Abstracts of Papers, 257th ACS National Meeting & Exposition, Orlando, FL, United States, Mar. 31-Apr. 4, 2019, pp. PMSE-0454, Conference; Meeting Abstract; Online Computer File, 2019.

* cited by examiner

*Primary Examiner* — Walter D. Griffin
*Assistant Examiner* — Cameron J Allen
(74) *Attorney, Agent, or Firm* — Hoffmann & Baron, LLP (57) ABSTRACT

A photodynamic composite including a porphyrin having four quaternized nitrogens, wherein the porphyrin is covalently bonded to a polymer containing reactive amines covalently bonded to a solid-state support is claimed. A method for sanitizing contaminated water is claimed including exposing the contaminated water to the photodynamic composite, in the presence of light and oxygen, wherein, a sufficient quantity of singlet oxygen and super oxide anions is provided by the chemical reaction of the light and the photosensitizer to destroy the pollutants or pathogens present in the contaminated water and to oxidize organic contaminants into carbon dioxide and water; thereby rendering the water potable.

18 Claims, 2 Drawing Sheets

PHOTODYNAMIC CATIONIC PORPHYRIN COMPOSITES

CROSS-REFERENCE TO RELATED APPLICATION

This application claims priority from U.S. Provisional Application No. 62/887,808 filed Aug. 16, 2019, which is incorporated herein by reference.

BACKGROUND OF THE INVENTION

Rapid increases in pollutant concentrations and the growing spread of harmful microbes in our environment are posing greater risks to human health. Air, soil and water have all been impacted. Sustainable access to safe and clean water has become a critical global challenge. Currently, more than 2.1 billion people lack access to safe drinking water, and the rate of waterborne transmitted diseases caused by bacteria, protozoa, viruses and parasitic pathogens continue to escalate. Simultaneously, human activity including growth in industry, population and agricultural waste cause contamination of world-wide water sources.

Conventional methods for disinfection such as filtration and boiling are ineffective for the removal of viruses and heat resistant bacteria. Other chemical purification techniques employ hazardous materials that themselves pose health and environmental hazards such as chlorine and chlorine salts used in chlorination, ion exchange resins incorporating bromine, oxidation using ozone or sodium hypochlorite and treatments that employ iodine. More demanding techniques involving electrochemical and ultraviolet sterilization are limited by their reliance on expensive equipment and access to electrical power sources.

There is a need for materials with disinfecting and decontaminating capabilities that are safe, efficient, cost effective and environmentally-friendly with improved antimicrobial and metal chelating properties, which can be used in water treatment.

SUMMARY OF THE INVENTION

The invention relates to a photodynamic composite including a porphyrin having four quaternized nitrogens, wherein the porphyrin is covalently bonded to a polymer containing reactive amines covalently bonded to a solid-state support. In a preferred embodiment, the porphyrin having four quaternized nitrogens is of formula I or II:

I

II wherein:
Y is independently

R is independently selected from the group consisting of —CH$_2$CH=CH$_2$, —CH$_2$CH$_2$OH, and —(CH$_2$)$_n$C(=O)OH;
n is an integer 1-16;
M is a divalent or trivalent metal ion; and
the porphyrin or formula I or II is charge balanced with the appropriate number of counter anions.

Preferably, the polymer containing reactive amines is polyethylenimine (PEI) or modified PEI. For modified PEI, then the PEI is preferably modified by acetylation, acylation, alkylation, quaternization, hydroxylation, succinylation, pegylation, or combinations thereof.

The solid-state support is preferably a metal oxide, inert material, or water insoluble salt. Metal oxides, include, but are not limited to, ZnO, MgO, AlO$_3$, SiO$_2$, TiO$_2$, and ZrO$_2$. Preferred solid-state supports include SiO$_2$, TiO$_2$, activated carbon, graphite, graphene oxide, charcoal, clay, zeolites, minerals, metal particles, silicates, carbonates, and sulfates.

When the porphyrin is of formula II, then M is preferably Fe, Pd, Zn, Cu, La, Lu, Y, In, Cd, Mg, Al, Ru, Ni, Mn, Ag, or Au.

Preferred counter anions include, but are not limited to, Br, I, F, Cl, sulfates, nitrates, perchlorates, sulfonates, and acetates.

The invention also relates to a method for sanitizing contaminated water including exposing the contaminated water to a photosensitizer comprising a porphyrin having four quaternized nitrogens covalently bonded to a polymer containing reactive amines covalently bonded to a solid-state support, in the presence of light and oxygen, wherein a sufficient quantity of singlet oxygen and super oxide anions is provided by the chemical reaction of the light and the photosensitizer to destroy the pollutants or pathogens present in the contaminated water and to oxidize organic contaminants into carbon dioxide and water, thereby rendering the water potable. The porphyrin having four quaternized nitrogens covalently bonded to a polymer containing reactive amines covalently bonded to a solid-state support is the photodynamic composite described above.

The pathogens destroyed by the photosensitizer include, but are not limited to, viruses, bacteria, protozoa, fungi, parasites, and combinations thereof.

Preferred values of n are 1, 2, 3, 4, and 5.

DETAILED DESCRIPTION

One aspect of the invention relates to a photodynamic composite including a photosensitizer. The photosensitizer is a molecule capable of generating reactive oxygen species upon light activation in the presence of molecular oxygen. The reactive oxygen species is in the form of singlet oxygen and superoxide anions which can kill viruses, bacteria, protozoa, and fungi, i.e., photodisinfection. The reactive oxygen species may also oxidize organic contaminates into carbon dioxide and water, i.e., photodecontamination.

In a preferred embodiment, the photosentizer is a porphyrin having four quaternized nitrogens. The preferred porphyrin is of formula I:

I

In formula I, Y is independently:

R is independently selected from the group consisting of —$CH_2CH=CH_2$, —$CH_2CH_2OH$, and —$(CH_2)_nC(=O)OH$ wherein n is an integer 1-16; and the porphyrin or formula I is charge balanced with the appropriate number of counter anions. Integers 1-16 are 1, 2, 3, 4, 5, 6, 7, 8, 9, 10, 11, 12, 13, 14, 15, and 16.

Independently means that each group Y and R may be represented by a different moiety. For example:

In another embodiment, the porphyrin is complexed to a metal. The porphyrin is of formula II:

II

In formula II, Y is as described above. M is a is a divalent or trivalent metal ion. For example, M includes, but is not limited to, Fe, Pd, Zn, Cu, La, Lu, Y, In, Cd, Mg, Al, Ru, Ni, Mn, Ag, and Au.

In each of formula I and II, the porphyrin is charge balanced with an appropriate number of counter anions. The anions may be monoanions, dianions, or trianions. Some examples of suitable anions include, but are not limited to, halides (F, Cl, Br, and I), sulfates, nitrates, perchlorates, sulfonates, acetates (e.g., perfluoroacetates).

Preferably, the porphyrin is covalently bonded to a polymer containing reactive amines. The polymer containing reactive amines is preferably polyethylenimine (PEI) or modified PEI. PEI is an amine-rich, water-soluble cationic polymer. It has antiviral properties and antimicrobial properties that can disrupt membranes and cause cell lysis. Additionally, PEI can be used for decontamination because it readily complexes with heavy metal ions.

The PEI of the invention is preferably branched. PEI of various molecular weights may be used. In one embodiment, the molecular weight of the PEI may be a value between about 100 to about 200,000. For example, the PEI may have a molecular weight of 1,800; 10,000; or 100,000.

The PEI may be modified in ways to provide various advantages. Modifications include, but are not limited to, acetylation, acylation, alkylation, quaternization, hydroxylation, succinylation, pegylation, or combinations thereof.

For example, branched PEI may be reacted with acetic anhydride in dimethyl sulfoxide (DMSO) and triethylamine (TEA) to form partially acetylated PEI. Partially acetylated PEI includes PEI with at least one hydrogen is replaced with an acetyl group. The reaction conditions may be adjusted to control the percentage of acetylation.

The polymer is covalently bound to a solid-state support. The solid-state support is preferably a metal oxide, inert material, or water insoluble salt. Examples of metal oxides include, but are not limited to, ZnO, MgO, AlO$_3$, SiO$_2$, TiO$_2$, and ZrO$_2$. Examples of inert materials include, but are not limited to, charcoal, clay, zeolites, minerals, and metal particles. Examples of water insoluble salts include, but are not limited to, silicates, carbonates, or sulfates. Preferred solid-state supports include SiO$_2$, TiO$_2$, activated carbon, graphite, and graphene oxide.

The polymer may be bound to the solid-state support using various methods known in the art. In one method, functionalization may be achieved by silanizing with either (3-Aminopropyl)trimethoxysilane (APTMS) or (3-Glycidyloxypropyl)trimethoxysilane (GPTMS). With APTMS, glutaraldehyde is used as a linker to covalently link the PEI polymer. When GPTMS is used, no linker is necessary. TEA may be added to help facilitate PEI amine reactivity.

The solid-state supported PEI may then be covalently attached to the porphyrin by various carbodiimide coupling reagents, e.g., (1-ethyl-3-(3-dimethylamino) propyl carbodiimide, hydrochloride (EDC)/N-hydroxysuccinimide (NHS) coupling.

Another aspect of the invention relates to a method for sanitizing contaminated water using the photodynamic composite of the invention, i.e. photosensitizer. The method includes exposing the contaminated water to the photodynamic composition, in the presence of light and oxygen, wherein a sufficient quantity of singlet oxygen and super oxide anions is provided by the chemical reaction of the light and the photosensitizer to destroy the pollutants or pathogens present in the contaminated water and to oxidize organic contaminants into carbon dioxide and water, thereby rendering the water potable.

The photodynamic composite is as described above. The pathogens are viruses, bacteria, protozoa, fungi, parasites, or combinations thereof. The pollutants are organic contaminants. The light may be any light including, but not limited to, sunlight, UV light, and white light.

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

A list following the word "comprising" is inclusive or open-ended, i.e., the list may or may not include additional unrecited elements. A list following the words "consisting of" is exclusive or closed ended, i.e., the list excludes any element not specified in the list.

Examples have been set forth below for the purpose of illustration. The scope of the invention is not to be in any way limited by the examples set forth herein.

EXAMPLES

Example 1. Synthesis of H$_2$MTPYP4

The base porphyrin on which alkylation was performed, H$_2$mTPyP4, was synthesized according to the group's procedure, which incorporates aspects of both the Lindsey and Adler-Longo methods. Scheme 1 below illustrates the basis of this synthesis.

Scheme 1. Synthesis of H$_2$mTPyP4.

1. Propionic acid Reflux, 1.5 h
2. DDQ, CHCl$_3$ Reflux, 30 min

Equimolar amounts (0.12 M) of freshly distilled pyrrole and 4-pyridine-carboxaldehyde were dissolved in 500 mL of propionic acid. This resulted in a reactant concentration of 0.24 M. This reaction mixture was refluxed for 1.5 hours, and then cooled to room temperature. To this, 3 equivalents of distilled water were added. The reaction mixture was then moved to a refrigerator for cooling. Sodium acetate trihydrate was added until the pH of the solution increased to approximately 4. This was then filtered and washed with water and methanol. The solid filtrate was collected and refluxed in methanol for 1 hour. The product was collected and oxidized by addition of 10% molar equivalence of DDQ and further refluxed in chloroform for 30 minutes. This mixture was poured through dry alumina and eluted with chloroform. The solid product was removed from the chloroform in vacuo and dried in an oven. Final purification of the H$_2$mTPyP4 was achieved through recrystallization from a chloroform/methanol system.

Example 2. Synthesis of H$_2$MTCMEPYP.4Br$^-$

A 100 mg portion of H$_2$mTPyP4 is added to a flask with 5 mL of anhydrous DMF. After an active purge with nitrogen, the reaction mixture is heated to 95° C. for 30 minutes with continuous stirring. Bromoacetic acid is added in 40 times molar excess (dissolved in minimal DMF) dropwise and the mixture is heated at 110° C. for 4 hours. The reaction is illustrated below in Scheme 2.

Scheme 2. Synthesis of H$_2$mTCMePyP4·4Br$^-$.

H$_2$mTPyP4

H2mTCMePyP4

The progress of the reaction is monitored by partitioning aliquots in chloroform/water and by thin-layer chromatography using an 8:1:1 water/acetonitrile/saturated potassium nitrate mobile phase. The reaction mixture is filtered hot by vacuum filtration, washed thoroughly with chloroform, and then collected in methanol and dried in vacuo. Purification is performed via recrystallization from a water/acetone solvent system.

Alternatively, the reaction is stopped and cooled to room temperature when monitoring indicated it has progressed sufficiently. The reaction mixture is cooled to room temperature, then filtered through a glass frit and washed with chloroform. The solid is collected and dried, and then recrystallized from water/acetone, chilled to 0° C. overnight, and then filtered and collected via vacuum filtration.

Example 3. Synthesis of H$_2$MTCHEPYP.4Br$^-$

A 100 mg portion of H2mTPyP4 is added to a flask with 5 mL of anhydrous DMF. After an active purge with nitrogen, the reaction mixture is heated to 95° C. for 30 minutes with continuous stirring. Bromohexanoic acid is added in 40 times molar excess (dissolved in minimal DMF) dropwise and the mixture is heated at 95° C. for 96 hours. The reaction is illustrated below in Scheme 3.

Scheme 3. Synthesis of H$_2$mTCHePyP4·4Br$^-$.

-continued

H₂mTCHePyP4

The progress of the reaction is monitored by partitioning aliquots in chloroform/water and by thin-layer chromatography using an 8:1:1 water/acetonitrile/saturated potassium nitrate mobile phase. The reaction mixture is filtered hot by vacuum filtration, washed thoroughly with chloroform, and then collected in methanol and dried in vacuo. Purification is performed via recrystallization from a water/acetone solvent system.

Alternatively, the reaction is stopped and cooled to room temperature when monitoring indicated it has progressed sufficiently. The reaction mixture is cooled to room temperature, then filtered through a glass frit and washed with chloroform. The solid is collected and dried, and then recrystallized from water/acetone, chilled to 0° C. overnight, and then filtered and collected via vacuum filtration.

Example 4. Absorbance of H₂MTPYP4

A 5 mg sample of H₂mTPyP was dissolved in 2 mL of chloroform (Alfa Aesar, lot #R08D708). The blank was recorded with chloroform, and a 1 cm quartz cell was used. The spectrum was recorded from 300 to 650 nm (chosen to exclude the absorbance of chloroform below 300 nm). The Soret band was located at 418 nm.

Example 5. Absorbance OF H₂MTCMEPYP.4Br⁻

A 5 mg sample of H₂mTCMePyP was dissolved in 2 mL of 18.2 MΩ ultrapure water. The blank was recorded with 18.2 MΩ ultrapure water, and a 1 cm quartz cell was used. The spectrum was recorded from 300 to 650 nm. The Soret band was located at 426 nm.

Example 6. Absorbance of H₂Mtchepyp.4Br⁻

A 5 mg sample of H₂mTCHePyP was dissolved in 2 mL of 18.2 MΩ ultrapure water. The blank was recorded with 18.2 MΩ ultrapure water, and a 1 cm quartz cell was used. The spectrum was recorded from 300 to 650 nm. The Soret band was located at 424 nm.

Infrared analysis of the H₂mTPyP was performed using the diamond-ATR attachment for the Infrared Spectrometer and 2 cm resolution.

Example 7. Retention Factor of H₂MTPYP

Several milligrams of H₂mTPyP4 were dissolved in chloroform (Alfa Aesar, lot #R080708) by gentle heating to 50° C., then cooled to room temperature. Thin layer chromatography (TLC) of H₂mTPyP was performed using a 1 inch wide strip of Sigma Aldrich foil-backed paper (lot #BCBS2516V). The mobile phase used was a freshly prepared 8:1:1 acetonitrile:water:saturated potassium nitrate. The retention factor was determined to be 0.697. Under long-wave UV light exposure, the analyte is seen to fluoresce a bright pink color.

Example 8. Retention Factor of H₂MTCMEPYP.4Br⁻

Several milligrams of H₂mTCMePyP4 were dissolved in methanol. Thin layer chromatography (TLC) of H₂mTCMePyP was performed using a 1-inch wide strip of Sigma Aldrich foil-backed paper (lot #BCBS2516V). The mobile phase used was a freshly prepared 8:1:1 acetonitrile:water:saturated potassium nitrate. The retention factor was determined to be 0.05. Under long-wave UV light exposure, the analyte is seen to fluoresce a bright pink color.

Example 9. Retention Factor of H₂MTCHEPYP.4Br⁻

Several milligrams of H₂mTCHePyP4 were dissolved in methanol. Thin layer chromatography (TLC) of H₂mTCHePyP was performed using a 1-inch wide strip of Sigma Aldrich foil-backed paper (lot #BCBS2516V). The mobile phase used was a freshly prepared 8:1:1 acetonitrile:water:saturated potassium nitrate. The retention factor was determined to be 0.05. Under long-wave UV light exposure, the analyte is seen to fluoresce a bright pink color.

Example 10. Fluorescence of H₂MTPYP

Fluorescence measurements were recorded using a Hitachi F-2500 Fluorescence Spectrophotometer. Chloroform was found to be an unsuitable solvent for this type of analysis due to its quenching of the porphyrins' fluorescence. THF was instead used to create a solution of concentration 2.9 mg/1090 µL (0.0043 M).

Example 11. Fluorescence of H₂MTCMEPYP.4Br⁻

Fluorescence measurements were recorded using a Hitachi F-2500 Fluorescence Spectrophotometer from 220 to 800 nm. The excitation scan was performed at 424 nm, and emission scan at 685 nm, with 5 nm slits. The concentration of H₂mTCMePyP4.Br⁻ was 1.3 mg/mL (0.0011M) in 18.2 MΩ ultrapure water. The maximum emission peak was at 685.5 nm.

Example 12. Silanization of Silica Gel with APTMS

Silica gel 60 (70-230 mesh) was washed with 1 M HCl and then with several portions of 18.2 MΩ H₂O. After drying, 5 g of silica gel was added to a 50 mL round bottom flask, to which 30 mL 18.2 MΩ H₂O and 750 µL APTMS were added. The reaction mixture was stirred at 50° C. for 90 minutes with an open air condenser. The silica was filtered by gravity and washed thoroughly with 18.2 MΩ H₂O, then sonicated twice for 30 minutes and dried in the oven to yield a white solid. This reaction is illustrated below in Scheme 4.

Scheme 4. Silanization of silica gel with APTMS.

Example 13. Silanization of Silica Gel with GPTMS

Silica gel 60 (70-230 mesh) was washed with 1 M HCl and then with several portions of 18.2 MΩ H₂O. After drying, 5 g of silica gel was weighed out into a 50 mL round bottom flask, to which 30 mL 18.2 MΩ H₂O and 750 µL GPTMS were added. The reaction mixture was stirred at 50° C. for 90 minutes with an open air condenser. The silica was filtered by gravity and washed thoroughly with 18.2 MΩ H₂O, then sonicated twice for 30 minutes and dried in the oven to yield a white solid. This reaction is illustrated below in Scheme 5.

Scheme 5. Silanization of silica gel with GPTMS.

Example 14. Addition of PEI to APTMS Silica Gel

A 2 gram portion of APTMS functionalized silica gel was added to a scintillation vial and 10 mL of 10% glutaraldehyde aqueous solution was added. The mixture was stirred in a sealed vial for 90 minutes at room temperature. The modified silica was filtered by gravity, and washed thoroughly with 18.2 MΩ H₂O, then acetone, and dried in the oven. A 100 µL portion of triethylamine was added prior to the addition of 10 mL of 10% aqueous solution of either 1,800 or 10,000 molecular weight PEI. This mixture was stirred in a sealed vial overnight. The hybrid composite material was filtered by gravity, washed thoroughly with 18.2 MΩ H₂O, sonicated twice for 30 minutes and then dried in the oven to yield a white solid. This process is illustrated below in Scheme 6.

Scheme 6. Addition of PEI to APTMS-functionalized silica gel.

Example 15. Addition of PEI to GPTMS Silica Gel

A 2 gram portion of GPTMS functionalized silica gel was added to a scintillation vial and a 100 µL portion of triethylamine was added prior to the addition of 10 mL of 10% aqueous solution of either 1,800 or 10,000 molecular weight PEI, depending on desired product. This mixture was stirred in a sealed vial overnight. The hybrid composite material was filtered by gravity, washed thoroughly with 18.2 MΩ H$_2$O, sonicated twice for 30 minutes to ensure unbound PEI was removed and then dried in the oven to yield a white solid. This process is illustrated below in Scheme 7.

Scheme 7. Addition of PEI to GPTMS-functionalized silica gel

Example 16. EDC/NHS-Coupling of H₂MTCMEPYP4.4BR⁻ to GPTMS Silica Gel

A 9 mg portion of mTCMePyP was dissolved in 4 mL MeOH. To this, 22 mg NHS dissolved in 100 μL of MeOH was added followed by 20 mg EDC dissolved in 100 μL MeOH. This solution was stirred for 30 minutes and then added to a vial containing 100 mg 2.5% GPTMS/PEI functionalized silica and 100 μL triethylamine. This mixture was stirred for 72 hours at room temperature in a sealed vial. The hybrid composite material was then filtered by gravity, washed extensively with 18.2 MΩ H₂O, sonicated in water and then dried in the oven, yielding a brown solid which fluoresces under UV light. This process is illustrated below in Scheme 8.

Scheme 8. EDC/NHS-coupling.

Example 17. Antibacterial Studies

Dose Dependence Studies

The antibacterial action of the porphyrin-functionalized silica, i.e., hybrid composite material, was assessed via a series of assays utilizing *S. epidermis* and *E. coli* bacteria. The porphyrin studied was H$_2$mTCMePyP4. A time-resolved study revealed killing of over 90% in 90 minutes by silica-grafted porphyrin. Bacterial targets had an initial concentration of ranging from log 5-6. They were subjected to increasing masses of silica alone, then PEI-grafted silica, and finally PEI/porphyrin-grafted silica. These trials were conducted in triplicate under room light and atmospheric conditions.

Figure 1:
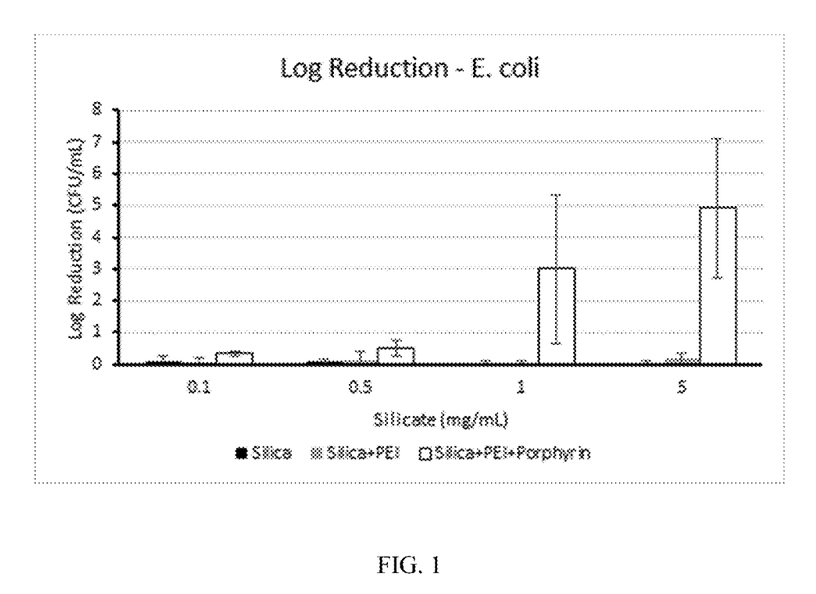
FIG. 1 Dose dependence microbiological study of *E. coli*.
Figure 2:
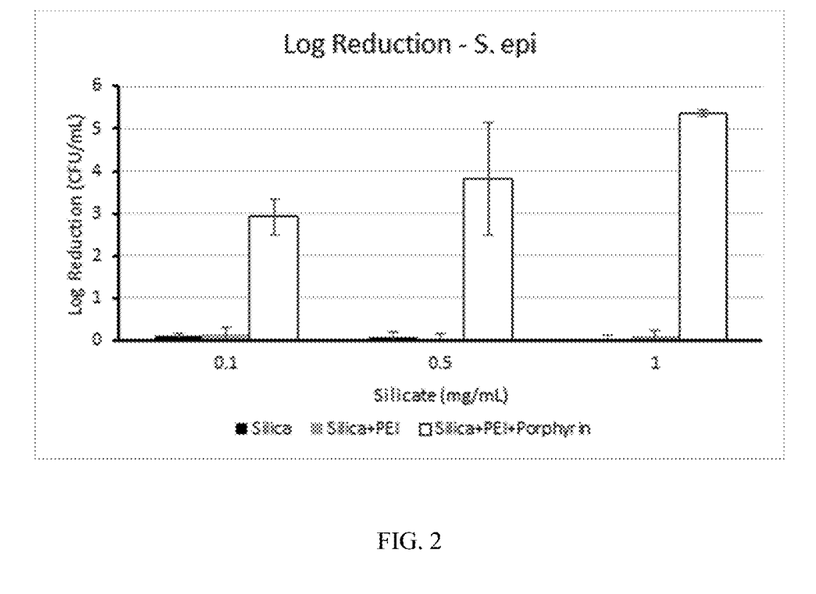
FIG. 2 Dose dependence microbiological study of *S. epidermis*.

Cytotoxicity of >log 5 reduction (99.999%) of *S. epidermis* was demonstrated using 1 mg of the composite material, and log 5 reduction of *E. coli* was demonstrated using 5 mg of the composite material. FIGS. 1 and 2 illustrate these findings.

The finding that 99.999% bacterial reduction is achieved by small quantities of the hybrid composite material is especially promising given the concentrations of bacteria used in this study were significantly greater than that of a typical contaminated water sample. Additionally, this study was conducted in a broth solution, an extremely amenable environment for bacterial growth and survival.

Time Dependence Studies

A time dependence study was conducted using a 1 mg sample of the composite material targeting initial log 5 to 6 bacterial concentrations. Aliquots were collected and analyzed in triplicate at 5 time points: 30, 60, 120, 180, and 240 minutes.

Figure 3:
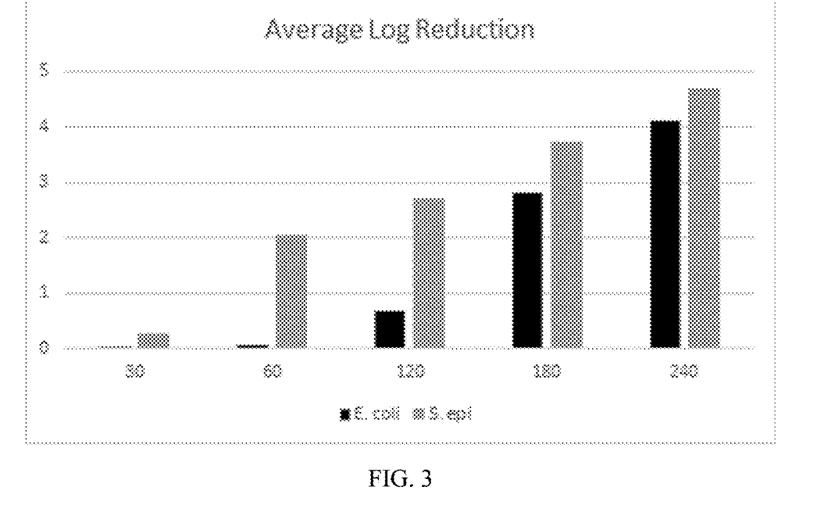
FIG. 3 Time dependence microbiological study. Average log reduction of bacteria vs. time.

The time dependence study shows a 99.99% cytotoxicity (log 4 reduction) of both the gram positive *S. epidermis* and gram negative *E. coli* within 4 hours of exposure to 1 mg of the composite material. FIG. 3 illustrates the average log reduction of bacteria versus time (min).

The PEI-grafted silica alone demonstrated killing at 10 mg, supporting the claim that the PEI polymer provides antibacterial properties. Silica alone did not result in any appreciable cytotoxicity. As with the dose-dependence studies, the conditions of the experiment provide important context for the observed bacterial reduction.

Example 18. Removal of Methyl Violet 2B

Figure 4:
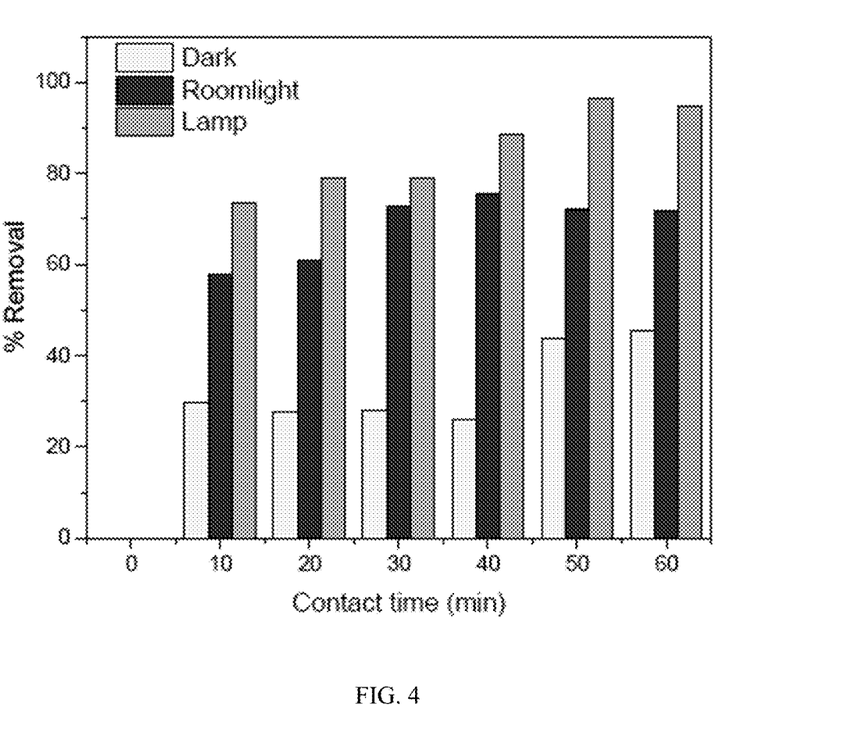
FIG. 4 Decomposition of Methyl Violet 2B dye over contact time.

FIG. 4 shows the decomposition of Methyl Violet 2B over time when subjected to the hybrid composite material while exposed to room light, a white light and no light. Approximately 100 mg of the composite was added to 50 mL of a purple aqueous solution of Methyl Violet 2B. The mixture was gently stirred while being exposed to room light, kept in the dark or irradiated with white light. ROS production caused degradation of the dye and in turn the loss of color from the solution. When subjected to white light the composite material removed greater than 90% of the methyl violet. Removal of the Methyl Violet 2B by the composite material in the dark demonstrates the ability of the PEI component of the composite to remove contaminants.

The invention claimed is:

1. A photodynamic composite comprising:
a porphyrin having four quaternized nitrogens of formula I or II,

I

II wherein:
Y is independently

R is independently selected from the group consisting of —CH$_2$CH=CH$_2$, —CH$_2$CH$_2$OH, and —(CH$_2$)$_n$C(=O)OH;
n is an integer 1-16;
M is a divalent or trivalent metal ion; and
the porphyrin of formula I or II is charge balanced with the appropriate number of counter anions; and
wherein the porphyrin is covalently bonded to a polymer containing reactive amines covalently bonded to a solid-state support.

2. The photodynamic composite according to claim 1, wherein the polymer containing reactive amines is polyethylenimine (PEI) or modified PEI.

3. The photodynamic composite according to claim 2, wherein the polymer containing reactive amines is modified PEI and the PEI is modified by acetylation, acylation, alkylation, quaternization, hydroxylation, succinylation, pegylation, or combinations thereof.

4. The photodynamic composite according to claim 1, wherein the solid-state support is a metal oxide, inert material, or water insoluble salt.

5. The photodynamic composite according to claim 4, wherein the solid-state support is a metal oxide selected from the group consisting of ZnO, MgO, AlO$_3$, SiO$_2$, TiO$_2$, and ZrO$_2$.

6. The photodynamic composite according to claim 4, wherein the solid-state support is SiO$_2$, TiO$_2$, activated carbon, graphite, graphene oxide, charcoal, clay, zeolites, minerals, metal particles, silicates, carbonates, or sulfates.

7. The photodynamic composite according to claim 1, wherein the porphyrin is of formula II and M is Fe, Pd, Zn, Cu, La, Lu, Y, In, Cd, Mg, Al, Ru, Ni, Mn, Ag, or Au.

8. The photodynamic composite according to claim 1, wherein the counter anions are Br, I, F, Cl, sulfates, nitrates, perchlorates, sulfonates, or acetates.

9. A method for sanitizing contaminated water comprising:
exposing the contaminated water to a photosensitizer comprising a porphyrin having four quaternized nitrogens covalently bonded to a polymer containing reactive amines covalently bonded to a solid-state support, in the presence of light and oxygen, wherein a sufficient quantity of singlet oxygen and super oxide anions is provided by the chemical reaction of the light and the photosensitizer to destroy the pollutants or pathogens present in the contaminated water and to oxidize organic contaminants into carbon dioxide and water, thereby rendering the water potable.

10. The method according to claim 9, wherein the porphyrin having four quaternized nitrogens is of formula I or II:

I

II wherein:
Y is independently

, or

R is independently selected from the group consisting of —CH$_2$CH=CH$_2$, —CH$_2$CH$_2$OH, and —(CH$_2$)$_n$C(=O)OH;
n is an integer 1-16;
M is a divalent or trivalent metal ion; and
the porphyrin of formula I or II is charge balanced with the appropriate number of counter anions.

11. The method according to claim 10, wherein the porphyrin is of formula II and M is Fe, Pd, Zn, Cu, La, Lu, Y, In, Cd, Mg, Al, Ru, Ni, Mn, Ag, or Au.

12. The method according to claim 10, wherein n is 1, 2, 3, 4, or 5.

13. The method according to claim 9, wherein the polymer containing reactive amines is polyethylenimine (PEI) or modified PEI.

14. The method according to claim 13, wherein the polymer containing reactive amines is modified PEI and the PEI is modified by acetylation, acylation, alkylation, quaternization, hydroxylation, succinylation, pegylation, or combinations thereof.

15. The method according to claim 9, wherein the solid-state support is a metal oxide, inert material, or water insoluble salt.

16. The method according to claim 15, wherein the solid-state support is a metal oxide selected from the group consisting of ZnO, MgO, AlO$_3$, SiO$_2$, TiO$_2$, and ZrO$_2$.

17. The method according to claim 15, wherein the solid-state support is SiO$_2$, TiO$_2$, activated carbon, graphite, graphene oxide, charcoal, clay, zeolites, minerals, metal particles, silicates, carbonates, or sulfates.

18. The method according to claim 9, wherein the pathogen is viruses, bacteria, protozoa, fungi, parasites, or combinations thereof.

* * * * *